April 20, 1965 W. D. KRAUSE Plant Pat. 2,496
PLUM TREE
Filed Dec. 30, 1963
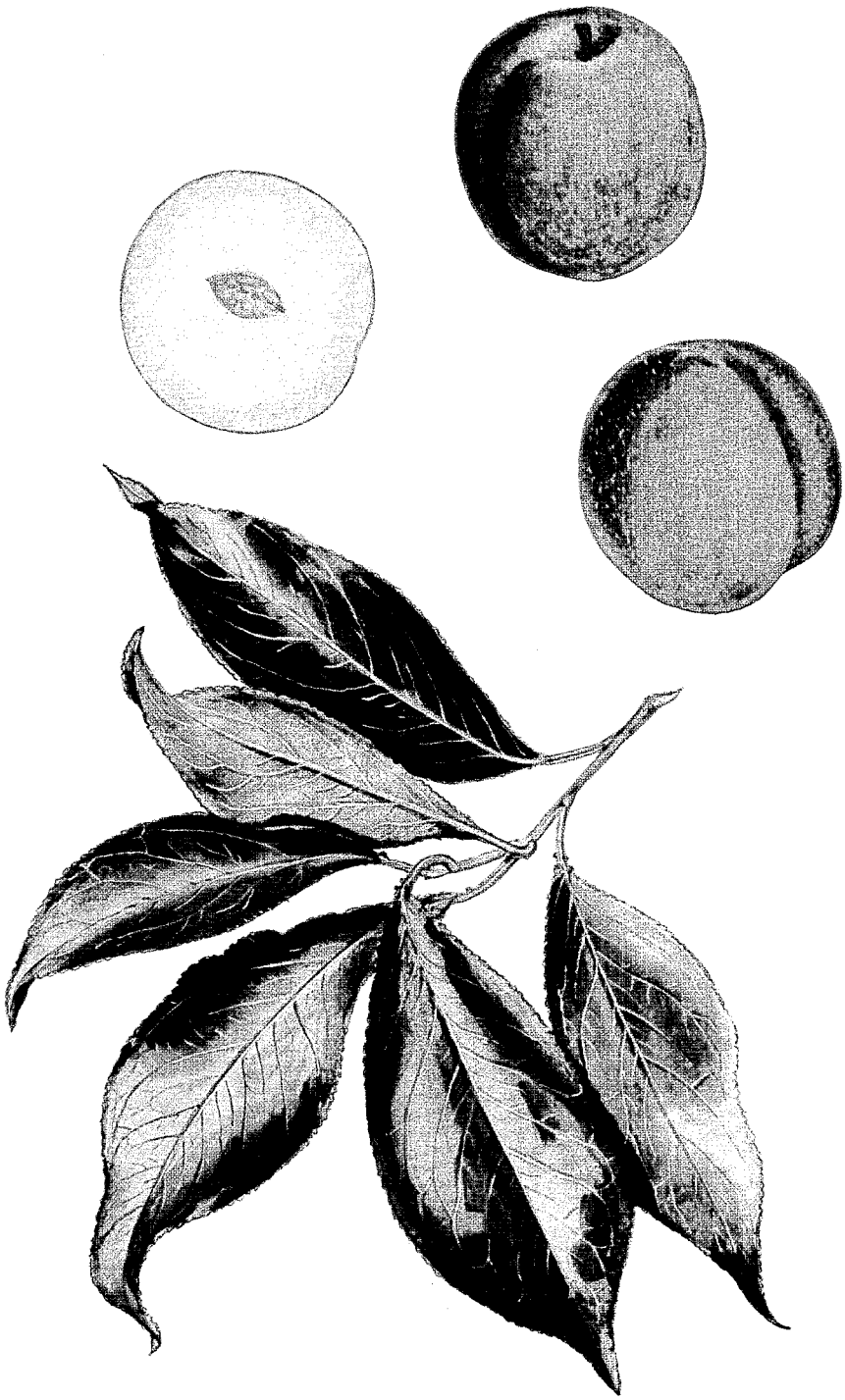
WITNESS
Leverett Boruszak
INVENTOR
Walter D. Krause
Webster & Webster
ATTORNEYS United States Patent Office Plant Pat. 2,496
Patented Apr. 20, 1965

2,496
PLUM TREE

Walter D. Krause, Fresno, Calif., assignor to Stribling's Nurseries, Inc., Merced, Calif., a corporation of California Filed Dec. 30, 1963, Ser. No. 334,679
1 Claim. (Cl. Plt.—38)

This invention relates to a new and distinct variety of plum tree which is desirably and advantageously characterized—both as to tree and fruit—as follows:

When propagated on a compatible rootstock, the tree is vigorous, thrifty, and healthy; the spreading habit or circumference of the tree being greater than the Santa Rosa but less than the Beauty.

The blossom is self-fertile, and the bloom is concurrent with other early varieties such as the Burmosa and Mariposa.

The fruit buds are well dispersed on both old and new growth, and in each year (even when other varieties under like growing conditions have failed) the present variety has set and matured a substantial crop of fruit.

The fruit is in initial harvest (on the average) five days earlier than the Beauty, while the last picking substantially coincides with the Burmosa. Such early initial harvest of the fruit of the present variety is of substantial commercial advantage and hence a major distinctive feature.

Additionally, the fruit has an excellent flavor and is of an attractive color; being a rose-purple shading to deep purple in full maturity.

The fruit in size, color, and shape most nearly resembles the Santa Rosa.

The herein claimed variety of plum tree was originated by me in the experimental orchard of a commercial nursery located near Merced, county of Merced, State of California, and of which nursery I am the research director.

The variety is a cross between the Santa Rosa, as the pollen parent, and the Burmosa, as the seed parent. Seed from such cross produced—among others—the present variety and which in maturity evidenced, while under careful and continuing observation, the described distinctive features.

Subsequent to origination of the variety, as above, I asexually reproduced it in the aforesaid experimental orchard; such reproductions having been accomplished by budding on peach and plum rootstocks. All such reproductions ran true to the original tree in all respects.

The drawing comprises an illustration, in color, of two whole fruits; another fruit cut in half to expose the flesh and stem; and a twig with leaves.

Referring now more specifically to the pomological details of this new and distinct variety of plum tree, the following is an outline description thereof; all major color plate identifications being by reference to Maerz and Paul Dictionary of Color, except where common terms of color definition are employed.

Tree:
- *Vigor.*—Moderate.
- *Growth.*—Sturdy trunk and limb development resulting in a well shaped vase-like tree.
- *Production.*—Very productive.

Trunk:
- *Form.*—Medium to slender.
- *Color.*—Slate to deep brown.

Branches:
- *Form.*—Medium to slender.
- *Texture.*—Medium.
- *Scaffold branches.*—Well dispersed with fruit-bearing twigs and hangers.
- *Color.*—Dull; slate to deep brown.

Lenticels:
- *Number.*—Medium.
- *Size.*—Medium.

Leaves:
- *Size.*—Average length—4". Average width—1¾".
- *Form.*—Oblanceolate, with an acuminate tip.
- *Thickness.*—Medium.
- *Texture.*—Smooth; glossy.
- *Occurrence.*—Appear at the close of blossoming time time and petal fall.
- *Color.*—Top side—deep rich green (23–H-7). Under side—flat lighter green (21–C–4). Vein structure—pale green.
- *Margin.*—Unevenly and finely crenated, glandular along the entire leaf margin.
- *Petiole.*—Medium thickness. Average length—9/16." Grooved from petiole base, extending into the basal end of the leaf.
- *Glands.*—Average number—four. Alternate in position; globose; green and reddish in color. Typically located—two on basal end of leaf with two or three on petiole near basal end of leaf. Stipules—average one per leaf, and 5/16" in length.

Flower buds:
- *Size.*—Average diameter—¼" to 5/16", suspended on a ⅜" stem.
- *Form.*—Obtuse; plump.

Flowers:
- *Blooming period.*—Date of full bloom: March 4, 1960; March 4, 1961; March 5, 1962; February 24, 1963.
- *Petals.*—White; profuse. Obtuse, slightly indented at apex. Average size—⅜" in length, and 5/16" in width.
- *Filaments.*—Silk-white, bearing lemon-yellow anthers; the pistil and anthers being of the same length.
- *Size.*—Average diameter of opened blossom—13/16".
- *Position.*—Flowers are grouped in loose clusters on twigs of one or more years old. Widely dispersed on current year's growth.

Fruit:
- *Maturity when described.*—Fully matured but firm and suitable for acceptance at local commercial markets.
- *Date of first picking.*—June 1, 1960; June 1, 1961; June 4, 1962; June 6, 1963.
- *Size.*—Average diameter axially—2 9/16". Average transversely in suture plane—2".
- *Form.*—Uniformly globose, slightly elongated at the apex.
- *Suture.*—Slightly indented and very shallow, extending from near the apex toward the greatest circumference of the fruit; and again a sharp medium suture line near the basal end, extending into the stem cavity.
- *Ventral surface.*—Well rounded, broad at base with both lips equal.
- *Cavity.*—Flaring abruptly, rounded with suture showing only on one side. Average depth—¼". Average width—3/16".
- *Base.*—Very evenly rounded in all dimensions.
- *Apex.*—Rounded to truncate, with no depression.

Skin:
- *Thickness.*—Medium.
- *Tenacity.*—Tenacious.
- *Flavor.*—Tangy, or slightly astringent.
- *Color.*—Rose-purple shading between (45–J–1) and (45–E–8), becoming a deeper purple at full maturity. Moderately flecked with yellowish (12–C–

6) lenticels. Abundantly overlaid with light blue bloom.

Flesh:

*Color.*—Light amber (10–H–4). Lightly streaked with white fibers about the pit cavity, and shading through orange to crimson (5–L–5) adjacent the skin.

*Surface of pit cavity.*—Light amber; flesh adheres to all surfaces of the pit.

*Amygdalin.*—Moderate.

*Juice.*—Moderate; rich flavor; very sweet, with a fruity aroma.

*Texture.*—Medium-firm.

*Fibers.*—Few; fine; tender; surrounding the pit cavity.

*Ripens.*—Evenly throughout entire fruit.

*Flavor.*—Spicy; subacid; pleasantly sweet.

*Aroma.*—Pronounced; spicy.

*Eating quality.*—Very good.

Stone:

*Type.*—Clingstone; fibers adhere to all surfaces of both the dorsal and ventral edges.

*Fibers.*—Short, extending into the flesh.

*Size.*—Small pit. Average length—9/16″. Average width—7/16″. Average thickness—5/16″.

*Form.*—Oblong, with an abrupt sharp point on the apex.

*Base.*—Straight.

*Hilum.*—Narrow and oblong.

*Apex.*—Acuminate, very sharply pointed.

*Sides.*—Equal, semi-rounded.

*Surface,*—Irregularly furrowed near the base, and pitted near the apex. Moderate pitting throughout.

*Ridges.*—Rounded, irregularly jagged near apex.

*Ventral edge.*—Thin, with wing toward apex.

*Dorsal edge.*—Narrow, with deep grooves on both sides.

*Ridges.*—Two lesser ridges on both sides of the dorsal edge.

*Pits.*—Elongated, with flat surface on the base.

*Color.*—Light amber (10–F–6).

*Tendency to split.*—Not common. Some cracking may occur when temperature falls below 32 degrees F. during blossom period and until blossom jackets fall.

Use: Fresh table fruit; commercial market, both local and long distance.

Keeping quality: Good. Fruit is firm and does not tend to break down readily. Keeps well in cold storage. Continues to ripen, with limited shrinkage, after picking. Retains good shelf life.

Shipping quality: Excellent.

The self-fertility of the blossom was substantiated by research activity in the previously mentioned experimental orchard. In particular, all parts of a number of fruiting twigs were isolated throughout the blossom period, depriving the blossoms of pollen contamination by insect and wind, resulting in a set of fruit within the isolation.

All of the herein identified previously known and existing varieties of plum tree are unpatented except the Mariposa, United States Plant Patent No. 111.

The tree and its fruit herein described may vary in slight detail due to climatic and soil conditions under which the variety may be grown; the present description being of the variety as grown in the Central Valley of California.

The following is claimed:

A new and distinct variety of plum tree substantially as illustrated and described, characterized by a vigorous, thrifty, and healthy tree having a greater spreading habit than the Santa Rosa but less than the Beauty; a self-fertile blossom in bloom concurrently with the Burmosa and Mariposa; fruit buds well dispersed on both old and new growth; an initial harvest of the fruit averaging five days earlier than the Beauty, and a final harvest coinciding with the Burmosa; and firm, well-flavored clingstone fruit having rose-purple to deep purple skin and light amber flesh which shades through orange to crimson adjacent the skin.

No references cited.

T. GRAHAM CRAVER, *Primary Examiner.*